(12) United States Patent
Masui et al.

(10) Patent No.: US 11,622,930 B2
(45) Date of Patent: Apr. 11, 2023

(54) ANTIMICROBIAL AGENT

(71) Applicants: Yoshiharu Masui, Yokkaichi (JP); Atsuko Tomida, Yokkaichi (JP)

(72) Inventors: Yoshiharu Masui, Yokkaichi (JP); Atsuko Tomida, Yokkaichi (JP)

( * ) Notice: Subject to any disclaimer, the term of this patent is extended or adjusted under 35 U.S.C. 154(b) by 3 days.

(21) Appl. No.: 17/236,055

(22) Filed: Apr. 21, 2021

(65) Prior Publication Data
US 2022/0087927 A1 Mar. 24, 2022

(30) Foreign Application Priority Data
Sep. 23, 2020 (JP) .............................. JP2020-158142

(51) Int. Cl.
| | | |
|---|---|---|
| *A61K 8/64* | (2006.01) | |
| *A61K 8/9794* | (2017.01) | |
| *A61K 8/44* | (2006.01) | |
| *A61K 8/41* | (2006.01) | |
| *A61Q 17/00* | (2006.01) | |
| *A61K 8/34* | (2006.01) | |

(52) U.S. Cl.
CPC ............ *A61K 8/9794* (2017.08); *A61K 8/345* (2013.01); *A61K 8/416* (2013.01); *A61K 8/44* (2013.01); *A61K 8/645* (2013.01); *A61Q 17/005* (2013.01); *A61K 2800/30* (2013.01); *A61K 2800/51* (2013.01)

(58) Field of Classification Search
CPC ...... A61K 8/9794; A61K 8/345; A61K 8/416; A61K 8/44; A61K 8/645; A61K 2800/30; A61K 2800/51; A61Q 17/005
See application file for complete search history.

(56) References Cited

FOREIGN PATENT DOCUMENTS

| | | |
|---|---|---|
| JP | 5314218 | 7/2013 |
| JP | 5314219 | 7/2013 |
| JP | 6057444 B1 | 12/2016 |
| JP | 2017-075094 A | 4/2017 |
| WO | WO2013/115061 A | 8/2013 |
| WO | WO2013/115062 A | 8/2013 |

*Primary Examiner* — Jessica Worsham
(74) *Attorney, Agent, or Firm* — Brie A. Crawford; Crawford Intellectual Property Law LLC (57) ABSTRACT

An antimicrobial agent contains amino acids extracted from grains as antimicrobial components. The antimicrobial agent includes a soybean-derived amino acid that functions as an antimicrobial component, extracted by separating solids from a grain solution to which a flocculent was added after heat treatment and filtration treatment. The antimicrobial composition also has butylene glycol, alkyldiaminoethylglycine hydrochloride, alkaline electrolyzed water, a cationic surfactant, an amphoteric ion surfactant, a nonionic surfactant, a chelating agent, and purified water.

2 Claims, 2 Drawing Sheets

Alkaline electrolyzed water →

Mycobacterium tuberculosis antibacterial agent →

Antibacterial Agent Stock Solution →

ANTIMICROBIAL AGENT

CROSS REFERENCE TO RELATED APPLICATIONS AND INCORPORATION BY REFERENCE

This application is a continuation in part of and claims priority to the previously filed Japanese Utility Patent Application No. JP2020-158142, titled ANTIBACTERIAL AGENT, with an application filing date of Sep. 23, 2020 in the Patent Office of Japan, by the same inventive entity. The entire contents of Patent Application No. JP2020-158142 are incorporated herein by reference to provide continuity of disclosure.

TECHNICAL FIELD OF THE INVENTION

The present invention is an antimicrobial agent containing amino acids extracted from grains as the antimicrobial ingredient.

BACKGROUND OF THE INVENTION

As commonly known, in November 2019, since the first confirmed case of the unexplained viral pneumonia in Wuhan, China, from the beginning of 2020 up until now, coronavirus infection caused by Severe Acute Respiratory Syndrome Coronavirus Type 2 (SARS-CoV-2) has been rampaging globally.

Due to the high latency of the coronavirus, in order to prevent human-to-human infection, there was no choice but to enforce lockdown and immigration restrictions to restrict the movement of people at home and abroad, including the delay of the Olympics, causing an unprecedented impact on the world in recent years.

Within japan, in order to prevent the spread of the coronavirus infection, we called for social distancing which recommended a behavioral pattern where individuals maintain a wider-than-usual physical distance between each other while living their daily lives.

One specific example of social distancing is that when waiting for one's turn to check out in a store, people who joined the queue maintained an approximate distance of two meters in front and behind them.

Furthermore, being hit by the coronavirus pandemic, from shop to shop in the town, disinfectants are installed everywhere at the entrances, and customers visiting the shops are encouraged to disinfect. Amidst such a large-scale spread of infection, the importance of disinfectants, which are normally be inconspicuous, is once again highlighted.

In addition to the coronavirus pandemic, in recent years, natural disasters, such as earthquakes, typhoons, and hurricanes, have been frequent in many parts of the world. Japan underwent major earthquakes such as the Kumamoto Earthquake and the Tottori Prefecture Chubu Earthquake in 2016 alone.

When such a large-scale disaster happens, infrastructures, such as the water supply, that supports the foundation of living, are damaged in a wide range and many households in the affected area often fall into water outage (discontinuation of living water). If living water is not available, many things normally enjoyed and taken for granted, such as washing hands or cleaning dishes after meals, became unimplementable, causing extraordinary inconvenience to those affected by the disasters.

Furthermore, when living in a shelter, people are forced to sleep in groups and multiple individuals share a temporary toilet. Therefore, naturally, toilet handles and faucet levels and handles are touched by a large number of people. That is, in the affected areas, it is often a reality that people are easily exposed to conditions prone to the spread of food poisoning and other diseases.

In situations where there is a shortage of living water, disinfectants with the purpose of hand hygiene (e.g., rubbing alcohol disinfectant containing ethanol) becomes quite useful.

In fact, products fulfilling such functions are frequently distributed in the real market (e.g., see Patent Document 1, 2 for reference).
[Patent Document 1] JP 5314218
[Patent Document 2] JP 5314219
[Patent Document 3] JP 6057444

Furthermore, the inventors of the present application have, as in Patent Document 3, acquired a patent for a preservation method and a body preservation device by redirecting the antimicrobial effect of amino acids extracted from grains from antimicrobial agents.

The preservative using the technique in Patent Document 3 has a very good antimicrobial effect against various bacteria and viruses (Document 3, Table 1, Paragraph [0043]). However, this preservative did not contain antimicrobial effect against *Mycobacterium tuberculosis* due at least in part to the fact that *Mycobacterium tuberculosis* has a cell wall that is rich in a unique lipid called mycolic acid and as a result, has a high resistance against disinfectants and drought.

However, even with *Mycobacterium tuberculosis*, it is possible to obtain an antimicrobial effect with the use of alcohol. Nonetheless, there are many people in this world who cannot use alcohol, such as the 1.6 billion Muslims in the world.

In this way, we must obtain a disinfectant/antimicrobial agent approved by Halal that can be used by Muslims, who account for approximately one in four people in the world. But, in order to be approved by Halal, the disinfectant cannot contain alcohol (ethanol) as an ingredient.

Thus, since containing alcohol (ethanol) as an ingredient is not accepted, it is extremely difficult to realize an antimicrobial agent that is Halal-approved and can also create antimicrobial effects against *Mycobacterium tuberculosis*.

The present invention, created in view of the above problems, has added to the existing antimicrobial/antiviral effects and has further antimicrobial effects against *Mycobacterium tuberculosis* and aims to provide an antimicrobial agent that is ethanol-free and thus approved by Halal.

SUMMARY OF THE INVENTION

An objective of the present invention is the provision of an antimicrobial agent that can reduce or eliminate microbes such as viruses and bacteria on the human body, clothing, and other objects and surfaces that are not part of the human body.

Another objective of the present invention is the provision of an antimicrobial agent that meets Halal certification.

Other objectives and advantages of the invention will become apparent from the description of the preferred embodiments herein.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

Thus, in order to solve the above problems, the antimicrobial agent according to the first embodiment of the present application is disclosed. It is an antimicrobial agent, in solution form, containing antimicrobial components that are amino acids extracted from grains.

As used herein, the components of the skin care composition are defined below. The components listed below are generic names. All capital letters are only used at the beginning of a sentence.

The first embodiment of the antimicrobial agent contains soybean-extracted amino acids functioning as the antimicrobial component, extracted by separating solids from a grain solution where a flocculent has been added after heat treatment and filtration treatment. It also contains the following components:
butylene glycol,
alkyldiaminoethylglycine hydrochloride,
alkaline electrolyzed water,
cationic surfactant,
amphoteric ionic surfactant,
nonionic surfactant,
chelating agent, and
purified water.

The following components make up the antimicrobial agent by percent weight of the total amount of the present antimicrobial agent. As used herein, "weight percent" or "percent by weight" and variations thereof refer to the concentration of a substance as the weight of that substance divided by the total weight of the composition and multiplied by 100. It is understood that, as used herein, "percent", "%", and "wt. %" are intended to be weight percent or percent by weight.
Antimicrobial Agent Stock Solution:

The antimicrobial stock solution is 0.76 wt % of the antimicrobial agent.
1) benzalkonium chloride: 0.20 wt %
2) propylene glycol: 0.20 wt %
3) ethylenediaminetetraacetic acid disodium salt: 0.10 wt %
4) sodium lauriminodipropionate: 0.05 wt %
5) glycine: 0.18 wt %
6) glycylglycine: 0.02 wt %
7) soybean-extracted amino acid: 0.01 wt %
8) purified water: 1.24 wt %
Additional Components:

The following components are added to the antimicrobial agent stock solution.
9) butylene glycol is added at 3.00 wt %
10) alkyldiaminoethylglycine hydrochloride is added at 0.20 wt %
11) alkaline electrolyzed water is added at 6.00 wt %
12) purified water is added at 88.8 wt %

| FIRST EMBODIMENT | |
|---|---|
| Components | Present in Weight Percent |
| benzalkonium chloride | 0.20 wt % |
| propylene glycol | 0.20 wt % |
| ethylenediaminetetraacetic acid disodium salt | 0.10 wt % |
| sodium lauriminodipropionate | 0.05 wt % |
| glycine | 0.18 wt % |
| glycylglycine | 0.02 wt % |
| soybean-extracted amino acid | 0.01 wt % |
| purified water | 1.24 wt % |
| butylene glycol | 3.00 wt % |
| alkyldiaminoethylglycine hydrochloride | 0.20 wt % |
| alkaline electrolyzed water | 6.00 wt % |
| purified water | 88.8 wt % |

In this antimicrobial agent, benzalkonium chloride serves as the cationic surfactant, propylene glycol serves and the nonionic surfactant, ethylenediaminetetraacetic acid disodium salt (hereinafter "EDTA2Na") serves as the chelating agent, and sodium lauriminodipropionate serves as the amphoteric ionic surfactant.

As described above, generally speaking, antimicrobial effects against *Mycobacterium tuberculosis* are realized with ethanol. On the other hand, the antimicrobial agent according to the first embodiment of the present application, while avoiding using ethanol to acquire Halal's certification, in order to realize the antimicrobial effect against *Mycobacterium tuberculosis*, employs (1) butylene glycol and (2) alkyldiaminoethylglycine hydrochloride. Hereinafter, butylene glycol and alkyldiaminoethylglycine hydrochloride components are referred to as "*Mycobacterium tuberculosis* antimicrobial agent" in conjunction.

Ethanol is a monohydric alcohol having one hydroxyl group. On the other hand, butylene glycol is a polyvalent alcohol obtained by adding hydrogen to the aldol condensate of acetaldehyde (bivalent alcohol: glycol). Here, butylene glycol is materially classified as alcohol while being outside of Halal certification's regulation and can thus be approved by Halal.

Since butylene glycol has two hydroxyl groups, it has very high hygroscopicity and water retention due to the influence of the hydroxyl groups. Also, since butylene glycol can extract both water-soluble components and oil-soluble components, a general use of butylene glycol is as an extraction solvent for plant extracts.

Butylene Glycol's Minimum Growth Prevention Concentration

In another aspect, measured data on butylene glycol and ethanol's minimum growth prevention concentration (MIC. Unit: %) against various bacteria was disclosed by Mikimoto Pharmaceutical Co., Ltd. in 2012.
(1) For *Staphylococcus aureus* (*Staphylococcus aureus*: Sa), butylene glycol's MIC was "16%", and ethanol's MIC was "9%".
(2) For Purmonia (*Pseudomonas aeruginosa*: Pa), butylene glycol's MIC was "8%", and ethanol's MIC was "5%".
(3) For *E. coli* (*Escherichia coli*: Ec), butylene glycol's MIC was "10%", and ethanol's MIC was "5%".
(4) For *Candida* (*candida* albicians: Ca), butylene glycol's MIC was "14%", and ethanol's MIC was "7%".
(5) For Koji mold (asprogillus *brasiliensis*: Ab), butylene glycol's MIC was "18%", and ethanol's MIC was "5%".

In addition, the experimental conditions at that this time were as follows:
Place 20 grams of sample (butylene glycol or ethanol) in a sterile container, inoculate and mix 0.2 ml of microbial suspension adjusted to $10^7$-$10^8$ pieces per milliliter. Take out a portion every other week and measure the number of live bacteria based on MIC.

As described above, butylene glycol's antimicrobial activity is slightly worse than ethanol's. Therefore, it cannot achieve the same level of antimicrobial effect as ethanol unless the concentration is higher than ethanol. However, even with butylene glycol alone, if the concentration is set to the minimum inhibitory concentration (MIC) or higher, the antimicrobial effect itself against various bacteria will be exhibited.

Incidentally, the above experiment by Mikimoto Pharmaceutical Co., Ltd. used a microbial suspension adjusted to $10^7$ to $10^8$ per ml. When the number of microorganisms present per ml is smaller, it is considered that even a butylene glycol solution with a concentration lower than the above MIC measurement data still exerts an antimicrobial effect against the above-mentioned *Staphylococcus aureus* and other bacteria.

Thus, the antimicrobial agent of the present application is devised to exert an antimicrobial effect against *Mycobacterium tuberculosis* by adding butylene glycol as an alternative component to ethanol.

Furthermore, the antimicrobial agent of the present application added alkyldiaminoethylglycine hydrochloride as the other component that exerts an antimicrobial effect against *Mycobacterium tuberculosis*. It has been confirmed that alkyldiaminoethylglycine hydrochloride exhibits a bactericidal effect against Acid-fast bacilli such as *Mycobacterium tuberculosis* at a high concentration (0.2 wt %~0.5 wt %). Incidentally, alkyldiaminoethylglycine hydrochloride, as it has a lower toxicity to living bodies and has a degreasing effect, is generally used for the disinfection of articles and instruments, not for disinfection for the human body.

The antimicrobial agent of the present application not only added alkyldiaminoethylglycine hydrochloride alone, but also added butylene glycol to achieve a higher-than-ever antimicrobial effect against *Mycobacterium tuberculosis*.

By devising such an agent, high antimicrobial effect against *Mycobacterium tuberculosis* can be achieved. Furthermore, compared with the prior art of Patent Document 3, a wider antimicrobial spectrum including an antimicrobial effect against *Mycobacterium tuberculosis* becomes possible to be realized.

Furthermore, the antimicrobial agent of the present application adopts butylene glycol as a substitute component for ethanol, which makes it approvable by Halal.

Incidentally, as described above, for alkyldiaminoethylglycine hydrochloride to exert a bactericidal effect against *Mycobacterium tuberculosis*, it needs to be added in a proportion of about 0.2 wt %-0.5 wt %.

Here, alkyldiaminoethylglycine hydrochloride has a low toxicity to the human body and has a degreasing effect, and thus tends to be shunned for the purpose of disinfecting the human body.

Nonetheless, in the present invention, by adding butylene glycol, which has an antimicrobial effect against *Mycobacterium tuberculosis*, the blending amount of alkyldiaminoethylglycine hydrochloride with higher antimicrobial strengths is suppressed to a relatively lower proportion (specifically, 0.2 wt %).

Incidentally, the reduced antimicrobial effect against *Mycobacterium tuberculosis* due to the suppressed blending amount of alkyldiaminoethylglycine hydrochloride is supplemented by the added butylene glycol.

Furthermore, butylene glycol is often used in cosmetics as a moisturizing ingredient for moisturizing human epidermis, and thus, even with alkyldiaminoethylglycine hydrochloride added, it is still possible to alleviate or reduce irritation to the user.

In addition, many conventional antimicrobial agents have alcohol (ethanol) added. But in Islam, the use of alcohol is prohibited not only, of course, for drinking, but also for disinfecting hands. As a result, this type of antimicrobial agent could not expand its user base among Islamic believers.

However, the antimicrobial agent 100 of the present application is an antimicrobial agent 100 made with an ethanol-free composition, it is possible to be approved by Halal (allowed by Islamic law), and thus the present antimicrobial agent 100 can be widely used by worshipers of various religions.

Therefore, in order to solve the above problems, the antimicrobial agent according to the second embodiment of the present application is used.

It is an antimicrobial agent in a solution form containing antimicrobial components that are amino acids extracted from grains, containing soybean-extracted amino acids functioning as the antimicrobial component extracted by separating solids from a grain solution where a flocculant has been added after heat treatment and filtration treatment. It contains the following:

butylene glycol,
alkyldiaminoethylglycine hydrochloride,
alkaline electrolyzed water,
benzalkonium chloride, which functions as a cationic surfactant,
sodium lauriminodipropionate, which functions as an amphoteric ionic surfactant,
polyoxy-propylene glycol, which functions as a nonionic surfactant,
ethylenediaminetetraacetic acid disodium salt (EDTA2Na), which functions as a chelating agent, and
purified water.

The following components make up the antimicrobial agent by percent weight of the total amount of the present antimicrobial agent.

Antimicrobial Agent Stock Solution:

The antimicrobial stock solution is 2.0 wt % of the antimicrobial agent.
1) benzalkonium chloride: 0.20 wt %
2) polyoxy-propylene glycol: 0.20 wt %
3) EDTA2Na: 0.10 wt %
4) sodium lauriminodipropionate: 0.05 wt %
5) glycine: 0.18 wt %
6) glycylglycine: 0.02 wt %
7) soybean-extracted amino acid: 0.01 wt %
8) purified water: 1.24 wt %

Additional Components:

The following components are added to the antimicrobial agent stock solution.
9) butylene glycol is added at 3.00 wt %
10) alkyldiaminoethylglycine hydrochloride is added at 0.20 wt %
11) alkaline electrolyzed water is added at 6.00 wt %

In addition, the composition was diluted with purified water at 88.8 wt % based on the total amount of the antimicrobial agent.

In this antimicrobial agent, benzalkonium chloride serves as the cationic surfactant, polyoxy-propylene glycol serves and the nonionic surfactant, ethylenediaminetetraacetic acid disodium salt serves as the chelating agent, and sodium lauriminodipropionate serves as the amphoteric ionic surfactant.

| SECOND EMBODIMENT | |
|---|---|
| Components | Present in Weight Percent |
| benzalkonium chloride | 0.20 wt % |
| polyoxy-propylene glycol | 0.20 wt % |
| EDTA2Na | 0.10 wt % |
| sodium lauriminodipropionate | 0.05 wt % |
| glycine | 0.18 wt % |
| glycylglycine | 0.02 wt % |
| soybean-extracted amino acid | 0.01 wt % |
| purified water | 1.24 wt % |
| butylene glycol | 3.00 wt % |
| alkyldiaminoethylglycine hydrochloride | 0.20 wt % |
| alkaline electrolyzed water | 6.00 wt % |
| purified water | 88.8 wt % |

As described above, generally speaking, antimicrobial effects against *Mycobacterium tuberculosis* are realized with ethanol. On the other hand, the antimicrobial agent according to the second embodiment of the present application, while avoiding using ethanol to acquire Halal's certification, in order to realize the antimicrobial effect against *Mycobacterium tuberculosis*, employs (1) butylene glycol and (2) alkyldiaminoethylglycine hydrochloride.

The surfactant used by the antimicrobial agent 100 of the present invention can be any general surfactant as long as it has an antimicrobial function.

One of the specific examples of the cationic surfactant mentioned is "benzalkonium chloride", which exhibits bactericidal properties by denaturing proteins in bacterial cell membranes.

Moreover, "sodium lauriminodipropionate" is mentioned as an example of an amphoteric ion surfactant with an antimicrobial function.

Furthermore, "polyoxy-propylene glycol" is mentioned as an example of a nonionic surfactant with an antimicrobial function.

Due to the high permeability of the surfactant, the antimicrobial agent 100 can efficiently permeate the antimicrobial object.

Furthermore, the chelating agent (those that form complex ions with metal ions by coordinate covalent bonds) added to the antimicrobial agent 100 is ethylenediaminetetraacetic acid disodium (EDTA2Na). Zinc is necessary for enzymes to work during bacterial reproduction. Nonetheless, since the addition of ethylenediaminetetraacetic acid disodium salt (EDTA2Na) blocks the metal ionization of zinc and the enzyme do not act, cell division cannot be performed, and thus the growth of bacteria can be suppressed.

Incidentally, when the antimicrobial agent 100 is applied or sprayed, it may adhere to the clothes and other items worn. In such a case, if chlorine-based disinfectant is used, clothing and covers may be whitened not only by the bactericidal and antimicrobial actions, but also by chlorine's bleaching effect.

However, the antimicrobial agent 100 of the present application is confirmed to not cause discoloration or color change according to the result after the discoloration/color-change test by spraying on dyed fabric products.

Therefore, discoloration (bleaching) can be prevented even if the present antimicrobial agent 100 adheres to the user's clothing or the like.

Furthermore, since antimicrobial agent 100 does not decolor (bleach) even if it adheres to the clothes, it is also possible to spray the antimicrobial material 100 on the user's clothes for antimicrobial purposes.

Hereinafter, the antimicrobial agent of the present invention will be described with reference to FIGS. 1 and 2.

The antimicrobial agent according to the first and second embodiments of the present invention is an example of a solution antimicrobial agent containing amino acids extracted from grains as the antimicrobial component.

Figure 1:
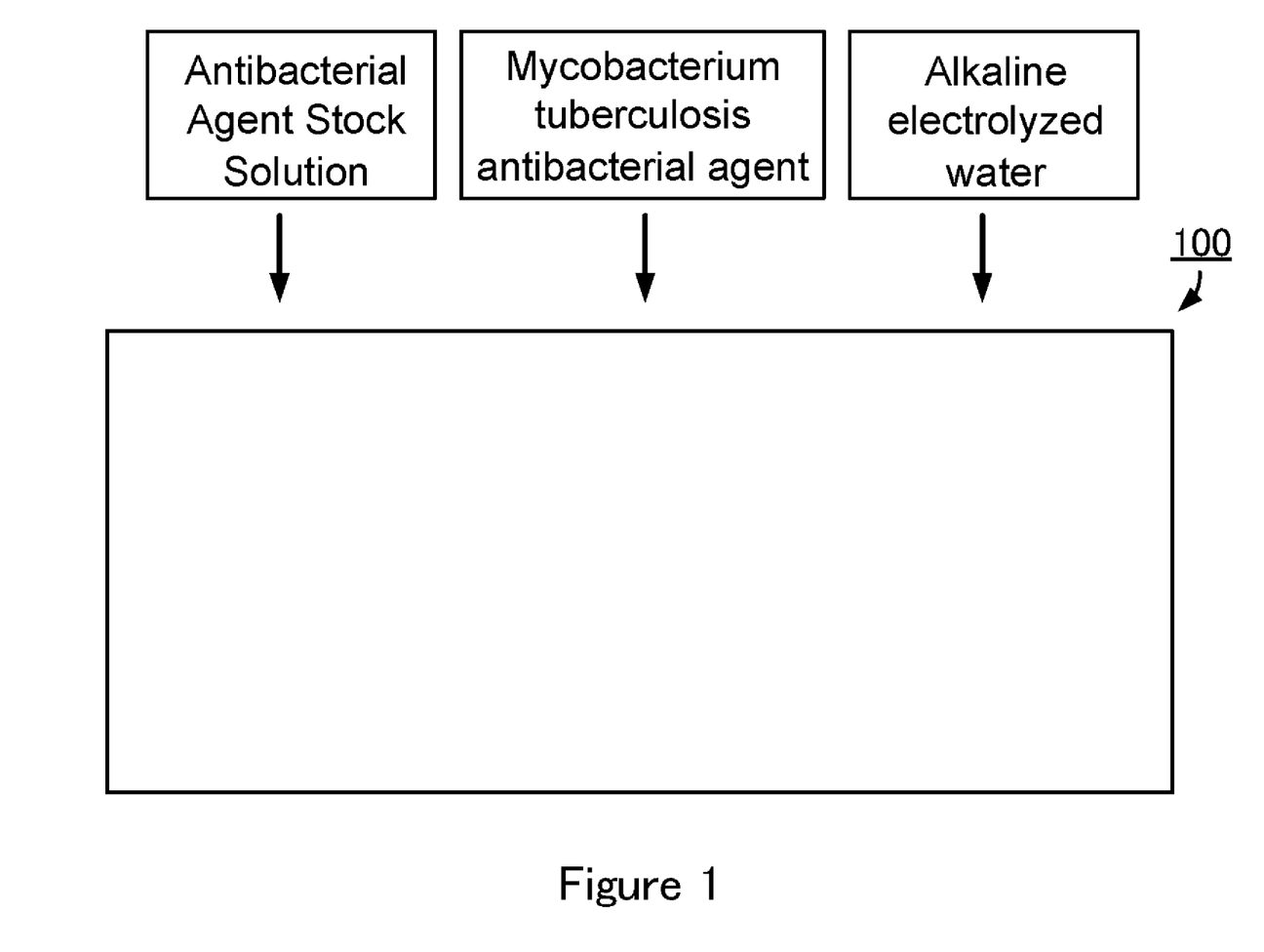
FIG. 1 depicts a schematic view indicating the composition of the antimicrobial agent according to the embodiment of the present invention.

As shown in FIG. 1, the antimicrobial agent 100 of the present application contains antimicrobial agent stock solution, a *Mycobacterium tuberculosis* antimicrobial agent, and alkaline electrolyzed water.

These three compositions are diluted with purified water.

Antimicrobial Agent Stock Solution

In order to produce the present antimicrobial agent 100 of the second embodiment, an antimicrobial agent stock solution with a higher concentration of antimicrobial components than the proper concentration is used. This antimicrobial agent stock solution uses [2.00 wt %] of the total amount of the present antimicrobial agent 100.

The antimicrobial agent stock solution contains soybean-extracted amino acids, surfactant (cationic surfactant, amphoteric ionic surfactant, nonionic surfactant), and a chelating agent.

Among these is the soybean-extracted amino acids contained in mixed solution extracted by separating solids from a solution of grains to which a flocculant has been added after heat treatment and filtration treatment.

Specifically, the antimicrobial agent stock solution is composed of (1) benzalkonium chloride, (2) polyoxy-propylene glycol, (3) EDTA2Na (ethylenediaminetetraacetic acid disodium salt), (4) sodium lauriminodipropionate, (5) glycine, (6) glycylglycine, and (7) soybean-extracted amino acid.

These seven types of compositions account for [0.76 wt %] of the total antimicrobial agent 100 amount.

The antimicrobial agent stock solution is composed by diluting these seven types of composition (0.76 wt % of the total amount) with purified water (1.24 wt % of the total antimicrobial agent 100 amount). In other words, the antimicrobial agent stock solution accounts for [2.00 wt %] of the total antimicrobial agent 100 amount.

Furthermore, the antimicrobial agent 100, on top of the above-mentioned antimicrobial agent stock solution, further adds the following compositions (8) butylene glycol, (9) alkyldiaminoethylglycine hydrochloride, and (10) alkaline electrolyzed water.

These three compositions (8) to (10), in total, are added with an amount equivalent to [9.20 wt %] of the total antimicrobial agent 100 amount.

More specifically, butylene glycol is added at [3.00 wt %] of the total antimicrobial agent 100 amount.

And alkyldiaminoethylglycine hydrochloride is added at [0.20 wt %] of the total antimicrobial agent 100 amount.

Together, butylene glycol and alkyldiaminoethylglycine hydrochloride constitute a *Mycobacterium tuberculosis* antimicrobial agent that exerts an antimicrobial effect against *Mycobacterium tuberculosis.*

In other words, *Mycobacterium tuberculosis* antimicrobial agent accounts for [3.20 wt %] of the total antimicrobial agent 100 amount.

Furthermore, the alkaline electrolyzed water is added at [6.00 wt %] of the total antimicrobial agent 100 amount. This alkaline electrolyzed water's pH is 12.

The second embodiment of antimicrobial agent 100 contains antimicrobial agent stock solution (2.00 wt % of the total antimicrobial agent 100 amount), *Mycobacterium* tuberculosis antimicrobial agent (3.20 wt % of the total antimicrobial agent 100 amount), and 6.00 wt % of alkaline electrolyzed water.

These above-documented components (11.20 wt % in total) are filled into a spray bottle after diluted to the proper concentration with 88.80 wt % of purified water.

Incidentally, the final pH level of the second embodiment of antimicrobial agent 100 is 4.5.

Next comes the description of the components contained in the present antimicrobial agent 100.

First, compositions added to the antimicrobial agent stock solution constituting the antimicrobial agent 100 that play a significant role will be described.

Benzalkonium Chloride

Benzalkonium chloride exerts bactericidal properties by denaturing proteins in bacterial cell membranes. Benzalkonium chloride functions as a cationic surfactant.

Ethylenediaminetetraacetic Acid Disodium Salt

Ethylenediaminetetraacetic acid disodium (EDTA2Na) functions as a chelating agent chelating (complexing) metal ions. Therefore, EDTA2Na complexes and collects the $Mg^{2+}$ and $Ca^{2+}$, and softens the water.

In addition, zinc is required for the enzyme to work during bacterial growth. However, by the chelating agent EDTA2Na added inhibits the ionization of zinc and prevents the enzyme from working so that cell division cannot be performed, and the suppression of bacteria growth is thus realized.

Soybean-Extracted Amino Acid

The antimicrobial agent stock solution of the present application utilizes soybean extract (soybean-extracted amino acids).

Soybean-extracted amino acids indicate a broad antimicrobial spectrum and ensure the antimicrobial agent 100's antimicrobial and inactivation effect on various bacteria and viruses.

Incidentally, soybean contains essential amino acids that cannot be synthesized in the human body, such as tryptophan, lysine, methionine, phenylalanine, threonine, valine, leucine, isoleucine, and histidine.

The basic production method of the grain-derived extract (in this case, soybean-extracted amino acids) in the present antimicrobial agent 100 is as follows.

First, soak the beans with water (in this case, soybeans) and crush the beans after sufficiently absorbing water into porridge. Next, heat the bean solution (porridge) at around 100° C. for 10-20 minutes, then at around 80° C. for 20-60 minutes. Then, filter the solution and add purified water and a flocculant (an agent that collects and precipitates suspended fine particles into a larger mass) to the filtrate. After, heat the solution after the addition at around 100° C. for 20 to 60 minutes to isolate the solid matter.

The pH value of the solution containing soybean-extracted amino acid obtained through such a process is approximately [pH 5.0] (pH 4.6-pH 5.4).

Antimicrobial Effect/Virus Inactivating Effect by Undiluted Antimicrobial Agent

Hereinafter, the effect of the antimicrobial agent stock solution is described based on test results.

In this case, the antimicrobial agent stock solution (second embodiment), as described above, contains (1)benzalkonium chloride, (2) polyoxy-propylene glycol, (3) ethylenediaminetetraacetic acid disodium (EDTA2Na), (4) sodium lauriminodipropionate, (5) glycine, (6) glycylglycine, and (7) soybean-extracted amino acids.

Incidentally, the antimicrobial agent stock solution does not contain (8) butylene glycol, (9) alkyldiaminoethylglycine hydrochloride, and (10) alkaline electrolyzed water.

TABLE 1

| Virus Name | Test Start Time (CFU/ml) | Duration of Action | Result |
|---|---|---|---|
| Avian Influenza Virus (H5N3 Strain) | $log_{10}$ $EID_{50}$/0.2 ml $10^{7.5}$ | 10 min | ≤1.5 (Not found) |
| Avian Influenza Virus (H7N7 Strain) | $log_{10}$ $EID_{50}$/0.1 ml $10^{7.5}$ | 10 min | ≤0.5 (Not found) |
| Coronavirus (Avian infectious bronchitis virus) | $log_{10}$ $EID_{50}$/0.2 ml $10^{5.5}$ | 10 min | ≤0.5 (Not found) |
| SARS Virus | 5 × 106 $TCID_{50}$/ml | 5 min | Not found |
| Human Influenza Virus (H1N1 Strain) | $4.92 \times 10^4$ CFU/ml | 7 days | Not found |
| Enterohemorrhagic *Escherichia coli* O-157 | $1.8 \times 10^6$ | 5 min | Not found |
| *E. coli* | $2.6 \times 10^6$ | 5 min | Not found |
| *Legionella* fungus | $8.3 \times 10^6$ | 5 min | Not found |
| *Salmonella* | $1.0 \times 10^6$ | 1 min | Not found |
| Mold (5 strain) JIS Z2911 (1992) | Growth area exceeds ⅓ of the total | 28 days | No identifiable growth |

TABLE 2

| Virus Name | Test Start Time (CFU/ml) | Duration | Result |
|---|---|---|---|
| Feline calicivirus (Norovirus substitution) | $log_{10}$ $TCID_{50}$/ml $10^{7.0}$ | 5 min | <3.5 (Not found) |
| Bovine rhinovirus Type 2 (Foot-and-mouth disease virus substitution) | Log's index difference | 60 min | ≥2.75 |
| *Bacillius cereus* spore | $1.0 \times 10^4$ spore/ml | 1 min | Not found |
| *Bacillius subtilis* spores | $4.2 \times 10^5$ | 10 min | Not found |
| *Staphylococcus aureus* | Phenol index | 10 min | 39 |
| Classical swine fever | Phenol index | 10 min | 39 |
| *Pseudomonas aeruginosa* (ATCC15442) | Phenol index | 10 min | 9 |
| Methicillin-resistant *Staphylococcus aureus* | $1.1 \times 10^6$ | 5 min | Not found |
| *Pseudomonas aeruginosa* (IFO13257) | $1.0 \times 10^8$ | 5 min | Not found |
| White ringworm | $2.8 \times 10^2$ | 5 min | Not found |
| *Candida* | $2.0 \times 10^8$ | 5 min | Not found |
| *Acinetobacter baumani* | $1.4 \times 10^8$ | 1 min | Not found |

Incidentally, the $TCID_{50}$ (TCID: median Tissue Culture Infectious Dose) in Tables 1 and 2 described above is a measurement unit for the virus infectious titer referring to the concentration that infects 50% of cells when a virus diluent is inoculated into a test tube or the like to which cells have been cultured and attached in advance.

Again, in the same Tables 1 and 2, the unit for bacteria amount is [CFU (Colony Forming Unit)/ml], which represents the number of units capable (the number of bacteria in 1 ml) of forming colonies. Further, the phenol coefficient is the numerical value (an index of bactericidal power) compared with phenol's bactericidal power.

As seen in the above Tables 1 and 2, the present antimicrobial agent 100 is recognized to have an inactivation effect against various viruses such as avian infectious bronchitis virus and SARS coronavirus, which are a kind of coronavirus, human influenza virus, and avian influenza virus.

SARS (Severe Acute Respiratory Syndrome) coronavirus is a virus that causes severe acute respiratory syndrome.

For human influenza virus, a test was conducted using the H1N1 strain.

In addition, feline calicivirus is a substitute for norovirus (a virus that causes non-bacterial acute gastroenteritis) with similar properties.

Furthermore, as seen from Tables 1 and 2, the present antimicrobial agent 100 is recognized to also have an antimicrobial effect against bacteria against various bacteria including *Bacillus cereus* spores, *Staphylococcus aureus*, enterohemorrhagic *Escherichia coli* O-157, *Escherichia coli*, *Legionella*, and *Salmonella*.

Incidentally, *Bacillus cereus* spores are a bacterium that causes food poisoning and an indigenous bacterium in the intestinal tract. *Staphylococcus aureus* is a bacterium residing in the human skin, gastrointestinal tract (intestine), etc., and may cause epidermal infection, food poisoning, pneumonia, meningitis, sepsis, and the like.

Enterohemorrhagic *Escherichia coli* O-157 is a bacterium that can cause hemorrhagic colitis which is often infected from undercooked ingredients.

*Escherichia coli* is also often the causative bacteria of urinary tract infections.

*Legionella* is a perennial intracellular parasite containing species that can cause many legionellosis diseases, including *Legionella* pneumonia (Legionnaires' disease).

*Salmonella* is an intestinal bacterium containing typhoid fever, paratyphoid fever, or causes of infectious food poisonings.

Various viruses and bacteria, including those listed in Tables 1 and 2, are lurking in the human body and articles used by humans.

Therefore, during a pandemic such as the coronavirus disaster, it is suitable to disinfect items that are potentially touched by an unspecified number of people.

Additionally, in the event of a disaster, it is desirable to implement preventative measures against illness and food poisoning targeting disaster victims living together in shelters.

Here, the antimicrobial agent stock solution contained by the antimicrobial agent 100 of the present embodiment is recognized to have a significant antimicrobial effect/virus inactivating effect, it contributes to the prevention of food poisoning, and the spread of diseases in the disaster areas.

Anti-Mold Effect

Furthermore, the antimicrobial agent stock solution comprising the antimicrobial agent 100 of the present embodiment is confirmed to have an anti-mold effect that suppresses the growth of mold as seen from Table 1.

Deodorant Effect

Further, the antimicrobial agent stock solution added to the present antimicrobial agent 100 not only has a virus inactivating effect, but also a deodorant effect.

Putrefaction is the decomposition of biologically derived organic substances (particularly, nitrogen-containing organic substances such as proteins) by microorganisms such as bacteria.

Then, when food and the like petrifacts, the formation and decomposition of putrefactive amines (indole, ketone, etc.) leads to the emission of an unpleasant odor (mainly the odor of "ammonia" or "hydrogen sulfide").

Figure 2:
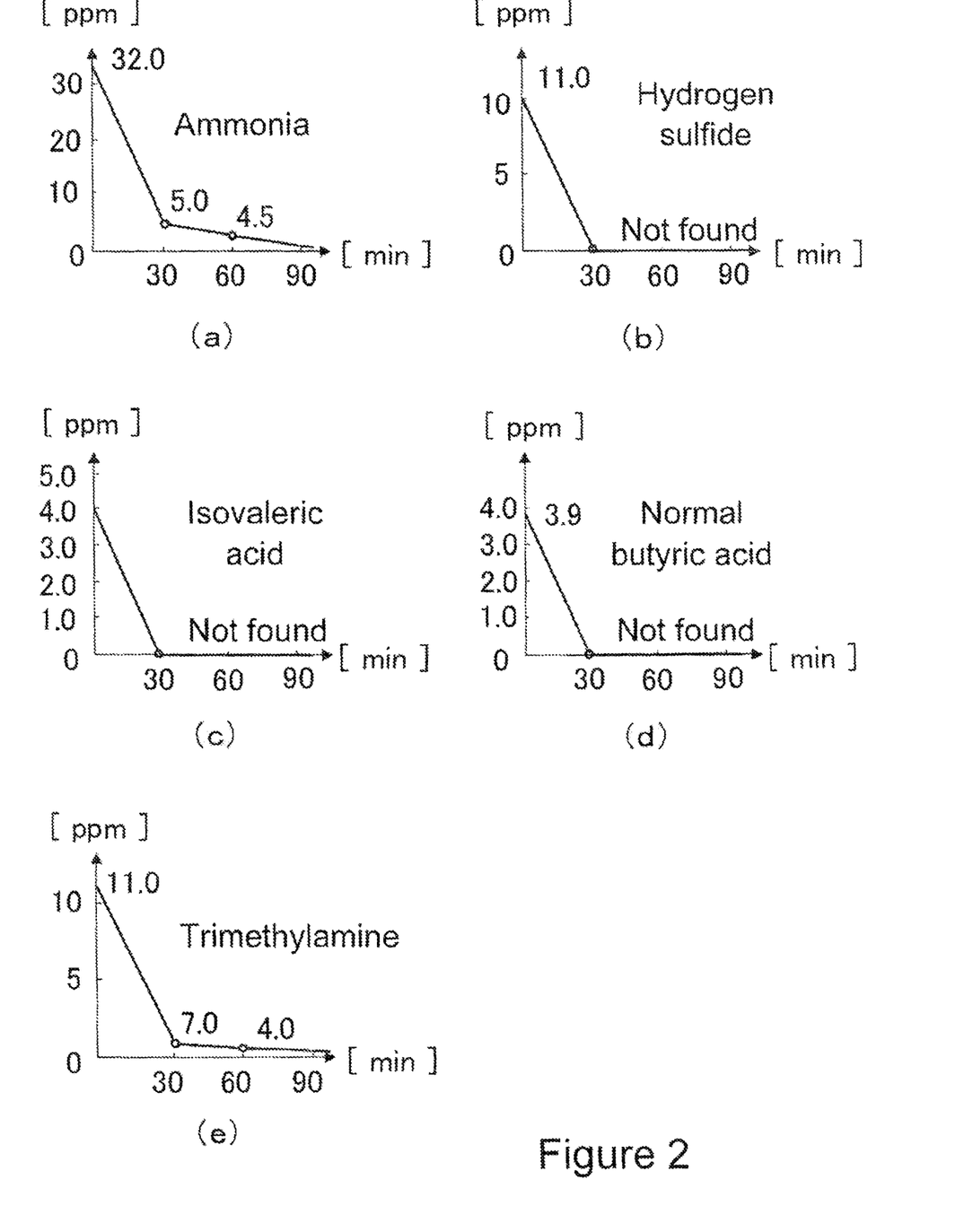
FIG. 2 depicts a schematic view showing the odor concentration with respect to elapsed time, where (a) is correspondent to ammonia, (b) is correspondent to hydrogen sulfide, (c) is correspondent to isovaleric acid, (d) is correspondent to normal butyric acid, and (e) is correspondent to trimethylamine.

However, it is confirmed via experiments that the antimicrobial agent stock solution has an excellent deodorizing effect against ammonia, as shown in FIG. 2(*a*), and hydrogen sulfide, as shown in FIG. 2(*b*).

In addition, this antimicrobial agent stock solution exerts outstanding deodorizing effect against Isovaleric acid (FIG. 2(*c*)), which is a typical component of livestock-type unpleasant odor among lower fatty acids, and normal butyric acid (FIG. 2 (*d*)).

Of the above two types of lower fatty acids, isovaleric acid is related to human foot sole odor, and normal butyric acid is related to a cause of bad breath.

Furthermore, the antimicrobial agent stock solution's deodorant effect is not only effective against human-derived odorous components, but also the putrid odor of fish, trimethylamine (a reduced osmoregulatory component trimethylamine-N-oxide contained in fish) (See FIG. 2(*e*)).

Ammonia, hydrogen sulfide, isovaleric acid, normal butyric acid, and trimethylamine used in the above experiments are all classified as substances regulated by the Offensive Odor Control Law.

Composition Having Antimicrobial Effect Against *Mycobacterium tuberculosis*.

Next, among the compositions added to the antimicrobial agent 100, the *Mycobacterium tuberculosis* antimicrobial agent exerting an antimicrobial effect against *Mycobacterium tuberculosis* will be described.

In the antimicrobial agent 100, the components exerting the antimicrobial effect against *Mycobacterium tuberculosis* are butylene glycol and alkyldiaminoethylglycine hydrochloride.

Butylene Glycol

Incidentally, when preparing a solution of an effective virus inactivating ingredient or a surfactant derived from soybean amino acid, active water alone or a mixture of active water and butylene glycol may be used as a diluent.

By doing so, the antimicrobial agent 100's permeability is enhanced, and the virus inactivating effect/antimicrobial effect and deodorizing effect can be efficiently exerted.

In addition, although it is inferior to ethanol's antimicrobial activity, butylene glycol still has a weak antimicrobial activity.

Therefore, by adding butylene glycol to the antimicrobial agent 100, it's possible to reduce the amount of alkyldiaminoethylglycine hydrochloride with a degreasing effect added.

By suppressing the amount of ingredients exerting powerful antimicrobial effects added, the antimicrobial agent 100 becomes possible to be used to disinfect the human body, and the irritation the antimicrobial agent 100 has on the user can be reduced.

Incidentally, a skin sensitization test was performed by the Maximization method to confirm whether or not an allergic reaction is induced when the antimicrobial agent 100 of the present application comes in contact with a living being's skin.

Specifically, 25 guinea pigs were used, and the samples were subcutaneously injected to induce sensitization. Then, after 72 hours, the guinea pigs where samples were stored were shaved, meanwhile the sample was sealed and pasted for 48 hours.

However, no allergic reaction was observed in all 25 guinea pigs when skin changes were observed at 48 h and 72 h after the sensitization induction.

Alkyldiaminoethylglycine Hydrochloride

Further, as the other ingredient that exerts antimicrobial effect against *Mycobacterium tuberculosis*, alkyldiaminoethylglycine hydrochloride is added to the antimicrobial agent 100 of the present application.

It has been confirmed that alkyldiaminoethylglycine hydrochloride exhibits a bactericidal effect against Acid-fast bacilli such as *Mycobacterium tuberculosis* at a high concentration (0.2 wt %~0.5 wt %). Incidentally, alkyldiaminoethylglycine hydrochloride is an ingredient with low toxicity to living organisms. Since it has a degreasing effect, one general use is to disinfecting articles and instruments instead of human bodies.

For alkyldiaminoethylglycine hydrochloride to exert a bactericidal effect against *Mycobacterium tuberculosis*, it is necessary to add it in a proportion of about 0.2 wt % to 0.5 wt %.

However, since the present antimicrobial agent 100 already adds butylene glycol, the blending amount of alkyldiaminoethylglycine hydrochloride, which enhances antimicrobial activity and has a degreasing effect, is suppressed to a relatively lower proportion (specifically, 0.2 wt %).

Further, by adding butylene glycol, it is possible to suppress the blending amount of alkyldiaminoethylglycine hydrochloride to a lower level, while still supplementing the antimicrobial effect against *Mycobacterium tuberculosis*.

It should also be noted that Patent Document 3, which is a conventional technique, makes it possible to support Halal certification.

Nonetheless, the art of Patent Document 3 has a wide antimicrobial spectrum yet does not have a bactericidal effect against *Mycobacterium tuberculosis*.

However, since the antimicrobial agent 100 of the present application has obtained a bactericidal effect against *Mycobacterium tuberculosis* while maintaining the same Halal certification as Patent Document 3, it is possible for it to realize a wider antimicrobial spectrum than that of Patent Document 3.

Additionally, the antimicrobial agent 100 is a solution. Thus, in actual use, it is desirable to fill a spray bottle with the antimicrobial agent 100 and spray it.

The spray bottle used here is not a general one that can be easily obtained. One specific example of spraying amount is to spray about 0.125 ml (125 μl) of liquid.

Growth Inhibitory Concentration of the Antimicrobial Agent of the Present Application To confirm the growth inhibitory concentration of the present antimicrobial agent 100, MIC (minimum inhibitory concentration) test was conducted.

The test results are shown below.

TABLE 3

| Virus Name | Minimum Inhibitory Concentration (μg/ml) | Dilution Rate |
|---|---|---|
| *E. coli* ATCC25922 | 3,905 | 1:256 |
| Enterohemorrhagic *Escherichia coli* O-157 | 1,950 | 1:512 |
| Proteus | 31,250 | 1:32 |
| *Salmonella* | 3,900 | 1:256 |
| Pathogenic coliform (EPEC) | 3,900 | 1:256 |
| Enterotoxic coliform | 7,800 | 1:128 |
| *Pseudomonas aeruginosa* (ATCC27853) | 7,800 | 1:128 |
| *Shigella* | 1,000 | 1:1024 |
| *Staphylococcus aureus* | 500 | 1:2048 |
| *Staphylococcus saprophytic* | 250 | 1:4096 |

TABLE 4

| Virus Name | Minimum Inhibitory Concentration (μg/ml) | Dilution Rate |
|---|---|---|
| *Staphylococcus albicans* | 3,900 | 1:256 |
| *Micrococcus luteus* | 500 | 1:2048 |
| *Pachirus Seleus* | 500 | 1:2048 |
| *Bacillus subtilis* | 3,900 | 1:256 |
| *Candida* | 1,000 | 1:1024 |
| *Listeria monocytogenes* | 500 | 1:2048 |
| Klebgera pneumoniae | 1,950 | 1:512 |
| *Vibro cholera* O1 | 3,900 | 1:256 |
| *Vibro cholera* O139 | 3,900 | 1:256 |
| *Vibro parahaemolyticus* | 3,900 | 1:256 |

The above MIC test provides insights for the minimum concentration of antimicrobial substances that blocks microorganisms (bacteria).

For the present antimicrobial agent 100, as indicated in Table 3, even when this antimicrobial agent 100 is diluted 2048 times (dilution ratio 2048), it is still possible to stop the growth of *Staphylococcus aureus*.

The MIC test is not conducted in a laboratory system where the antimicrobial agent 100 can directly act on the microorganism, but in an environment where each bacterium actually inhabits (the actual environment in which the antimicrobial agent 100 is used) so it is possible to confirm how much antimicrobial effect can be expected.

In an environment where each bacterium actually inhabits and where water and organic matter exists, even if the antimicrobial agent 100 is diluted and the effect of the antimicrobial agent 100 becomes inhibited, as long as it is within the dilution ratio shown in Tables 3 and 4, the antimicrobial effect can be effectively exhibited.

Mutagenicity Test

Generally speaking, the frequent use of a drug against the same bacteria can result in mutations in the surviving bacteria's genes, making them resistant to the drug.

The methicillin-resistant *Staphylococcus aureus* (MRSA) listed in Table 2 is a bacterium that causes nosocomial infections, etc., but also a typical bacterium with drug-resistance.

The inventor of the present application conducted a mutagenicity test (4 types of bacteria including *Salmonella*) using the antimicrobial agent 100 and confirmed that resistant bacteria did not occur.

Incidentally, the mutagenicity test is also a screening test used to confirm that the antimicrobial agent 100 is not carcinogenic.

Acute Inhalation Toxicity Test

Generally, when a disinfectant is sprayed, it is sometimes inhaled through the mouth or the nose.

The inventor of the present application conducted an acute inhalation toxicity test, whose results confirmed that no toxicity impairs respiration even if the antimicrobial agent 100 is inhaled.

Compliance with Food Sanitation Law Standards

To confirm that it is safe to use the antimicrobial agent 100 in food-related facilities, its suitability was confirmed in light of the standards of the Food Sanitation Law.

Specifically, the suitability of Standard No. 5 Cleaning Agent for Foods, Additives, etc. was confirmed according to the test method for arsenic/heavy metals.

The results confirmed that the present antimicrobial agent 100 does not contain arsenic/heavy metals and conforms to the safety test when used as a food cleaning agent.

Instrument Container Packaging Standard Test

Further, the present antimicrobial agent 100 is confirmed to conform to safety standards according to the standards of the Food Sanitation Law when used in packaging materials for food packaging. Specifically, results from material tests for the present antimicrobial agent 100 confirmed that no lead was used.

Further, the elution test for the present antimicrobial agent 100 confirmed that no heavy metal was eluted and that the elution amount of organic matter and oxides is below the standard.

The Effect of the Disinfectant of the Present Application Against Coronavirus

Further, to confirm the effect of the disinfectant of the present application against coronavirus, the disinfectant solution was provided as a test material and the test was conducted by entrusting the Kyoto Sangyo University Bird Flu Research Center (Director, Koichi Otsuki). The experimental results obtained is described below.

Virus Used

The virus used in the coronavirus inactivation effect confirmation test was the avian infectious bronchitis virus Nerima strain.

The virus strain was ingested in the allotonic cavity of an 8-day-old developing chicken egg (incubated with SPF (Specific Pathogen Free) fertilized eggs), cultured at 35° C. for 4 days, and then serous urine was collected and used as a viral solution.

Experimental Method

The experiment procedure was as follows.

Step 1. The test solution (disinfectant of the present application) and the virus solution were mixed at 9:1 or 1:1, respectively.

Step 2. After mixing, let sit and react under room temperature for 10 minutes.

Further, as the negative subject, instead of the test solution (disinfectant), mix phosphate buffer saline (PBS) and the viral solution and let sit and react under room temperature for 10 minutes.

Step 3. After the completion of reaction, serially dilute the reaction solution by 10 fold with phosphate buffered saline. Incidentally, for each dilution stage, take 2 milliliters at a time from the allantois cavity of 4 8-day-old growing chicken eggs.

Step 4. After culturing at 35° C. for 5 days, or, until the chicken embryo dies, open the eggs and determine whether there was virus growth based on whether dwarfing of the chicken embryo was present. Calculate the residual viral force value using REID and Muench method. Confirmation results of inactivating effect of the disinfectant of the present application on coronavirus.

Regarding the inactivation effect of the disinfectant 100 against coronavirus, when the present disinfectant 100 was acting in 9 times the amount of the virus solution, in other words, when the mixing ratio of the disinfectant 100 and the virus solution was 9:1, it was confirmed that the residual viral force value was reduced to approximately $1/100,000$ and below.

Further, when the test solution (disinfectant 100) acted with an equal amount of virus solution, in other words, when the mixing ratio of the disinfectant 100 and the virus solution was 1:1, it was reduced to about $1/100,000$.

In other words, the disinfectant 100 of the present application is confirmed to, at least, exert a high inactivation effect against chicken infectious bronchitis virus, is a type of coronavirus.

Therefore, it is believed that, by using the disinfectant 100 of the present application, a certain reducing effect against severe acute respiratory syndrome coronavirus type 2 (SARS-CoV-2) can be expected.

TABLE 5

| Test Solution: | | 1:1 | |
|---|---|---|---|
| Virus Solution | 9:1 | $1^{st}$ time | $2^{nd}$ time |
| Disinfectant | ≤0.5* | 0.5 | 0.5 |
| Negative Subject | 5.5 | 5.25 | 5.5 |

*Residual viral force value ($\log_{10}$ EID$_{50}$/0.2 ml)

Modification Example: Antimicrobial Component

The antimicrobial component of the antimicrobial agent 100 of this embodiment is not limited to soybean-derived amino acids alone, but could also use glycine/cysteine, which are components of proteins, glycylglycine, which is a peptide bond of two molecules of glycine, or any active plant- or animal-derived amino acid.

Incidentally, the antimicrobial agent 100 itself is prepared by blending a surfactant into this antimicrobial component.

Further, glycine cysteine glycylglycine also has a strong deodorizing action, when disinfecting by users of the antimicrobial agent, it relieves the discomfort derived from the odors released by the object being disinfected.

Although the present invention has been described above with reference to the embodiments, the present invention is not limited to the above embodiments. Various modifications that can be understood by those skilled in the art can be made to the structure and details of the present invention without departing from the gist of the present invention.

DESCRIPTION OF SYMBOLS

100 Antimicrobial Agent

The invention claimed is:

1. An antimicrobial agent composition comprising:
   a) amino acids at 0.01 percent by weight which are extracted from soybean grains, wherein the amino acids function as the antimicrobial agent;
   b) butylene glycol at 3 percent by weight;
   c) alkyldiaminoethylglycine hydrochloride at 0.20 percent by weight;
   d) alkaline electrolyzed water at 6 percent by weight;
   e) a cationic surfactant at 0.20 percent by weight;

f) amphoteric ionic surfactant at 0.05 percent by weight;
g) a nonionic surfactant at 0.20 percent by weight;
h) a chelating agent at 0.10 percent by weight;
i) glycine at 0.18 percent by weight;
j) glycylglycine at 0.02 percent by weight; and
k) purified water at 90.04 percent by weight.

2. The antimicrobial agent composition of claim 1, wherein:
   a) the chelating agent is ethylenediaminetetraacetic acid disodium salt;
   b) the cationic surfactant is benzalkonium chloride;
   c) the nonionic surfactant is propylene glycol; and
   d) the amphoteric ionic surfactant is sodium lauriminodipropionate.

* * * * *